(12) United States Patent
Kessler et al.

(10) Patent No.: US 9,725,294 B2
(45) Date of Patent: Aug. 8, 2017

(54) GASKET SECURING MEANS FOR A UNIVERSAL MANIFOLD

(71) Applicants: Justus Kessler, Lake Elsinore, CA (US); Jason Touhy, Winchester, CA (US)

(72) Inventors: Justus Kessler, Lake Elsinore, CA (US); Jason Touhy, Winchester, CA (US)

( * ) Notice: Subject to any disclaimer, the term of this patent is extended or adjusted under 35 U.S.C. 154(b) by 217 days.

(21) Appl. No.: 14/301,152

(22) Filed: Jun. 10, 2014

(65) Prior Publication Data
US 2015/0353339 A1 Dec. 10, 2015

(51) Int. Cl.
| | | |
|---|---|---|
| *B67D 7/06* | (2010.01) | |
| *B67D 7/02* | (2010.01) | |
| *B67D 7/36* | (2010.01) | |
| *G01N 30/04* | (2006.01) | |

(52) U.S. Cl.
CPC ............ *B67D 7/0288* (2013.01); *B67D 7/36* (2013.01); *G01N 30/04* (2013.01)

(58) Field of Classification Search
CPC ........ B67D 7/0288; B67D 7/36; G01N 30/00; G01N 30/04
USPC ................... 141/236, 244, 285–286
See application file for complete search history.

(56) References Cited

U.S. PATENT DOCUMENTS

| | | | | |
|---|---|---|---|---|
| 2,072,855 A | * | 3/1937 | Danver | F01M 3/00 123/196 M |
| 3,134,612 A | * | 5/1964 | Glasgow | F16L 17/04 277/612 |
| 3,498,310 A | * | 3/1970 | Hechler | A01C 23/042 137/218 |
| RE27,378 E | * | 5/1972 | Lohn | F02M 19/00 123/184.46 |
| 3,687,487 A | * | 8/1972 | Lindholm | F16L 21/065 138/89 |
| 4,893,962 A | * | 1/1990 | Komeyama | F16D 1/033 403/288 |
| 2001/0003652 A1 | * | 6/2001 | Freeman | B01L 7/52 435/286.5 |
| 2008/0017821 A1 | * | 1/2008 | Orban | F16L 21/035 251/149.6 |
| 2008/0038714 A1 | * | 2/2008 | Gao | B01L 3/502715 435/4 |
| 2011/0268832 A1 | * | 11/2011 | Gao | B01D 19/00 425/233 |
| 2012/0329681 A1 | * | 12/2012 | Gao | B01F 11/0071 506/33 |
| 2013/0158896 A1 | * | 6/2013 | Schintee | G01L 9/0001 702/41 |
| 2014/0080226 A1 | * | 3/2014 | Cauley, III | B01L 3/502784 436/180 |
| 2015/0083274 A1 | * | 3/2015 | Kessler | B67D 7/0288 141/236 |

* cited by examiner

*Primary Examiner* — Nicolas A Arnett

(57) ABSTRACT

The current invention teaches a universal manifold for delivering chemical liquids to a storage container. The universal manifold contains a universal mating system that enables a single manifold to attach to a number of variously sized storage containers that include a number of variously sized fill apertures. This enables the use of the same universal manifold for the delivery and collection of liquid chemical to the storage container at different times.

3 Claims, 4 Drawing Sheets

GASKET SECURING MEANS FOR A UNIVERSAL MANIFOLD

FIELD OF INVENTION

The present invention relates to chemical liquid storage containers that are used for delivering and collecting chemical liquid. More specifically the present invention discloses a universal manifold that enables the delivery and collection of chemical liquid by way of a storage container. The universal manifold includes a mating system and a gasket securing system that mates the universal manifold to a storage container whereby the universal manifold is enabled to mate with multiple types of storage containers having various sizes of fill apertures.

BACKGROUND OF THE INVENTION

High performance chemical liquid chromatography, also known as high pressure chemical liquid chromatography and HPLC, is a commonly used analytical procedure and machine which involves the use of a plurality of different chemical liquids whereby a plurality of different chemical liquids flow through the chromatograph to analyze the chemical composition of the plurality of different chemical liquids. HPLC also requires the use of a storage container in which, upon completion of the analytical procedure, the plurality of different chemical liquids is accumulated and stored. Furthermore it is common for the plurality of different chemical liquids to include at least one chemical liquid that is hazardous.

It is known in the art that a storage container for storing chemical liquids from an HPLC machine must be fully sealed to prevent the chemical liquids from evaporating into the atmosphere. This is even more important when a hazardous chemical liquid is used. Over time the hazardous chemical liquid will also evaporate into the atmosphere, and may come into contact or even be inhaled by humans and animals. Inhaling hazardous chemical liquid vapor is even more likely when the plurality of different chemical liquids is stored within an enclosed or semi-closed environment like a laboratory.

Caps and filtration systems that reside on the storage container in an effort to seal the storage container have been devised to reduce and even eliminate chemical liquid from evaporating into the environment. Over time, caps were further developed to enable the insertion of a supply tube in an effort to seal the storage container while still supplying chemical liquids. The purpose of the supply tube is to transport chemical liquids from the HPLC machine to the storage container when collecting. The supply tube was also designed to insert directly through a hole in the cap and into the storage container. Multiple holes in caps were then developed such that one storage container may receive a plurality of chemical liquids. Furthermore it was found that providing a means for securing the supply tube to the cap was desirable. Therefore ports were developed in the cap which often comprise of a threaded means to enable a secure method of attaching a supply tube to the cap.

Although the further developments in caps as described above have reduced and even eliminated hazardous chemical liquid from evaporating into the environment when using a storage container to accumulate and store chemical liquids from an HPLC machine or a machine that requires an accumulation and storage means for chemical liquids or solvents, the caps still have limitations.

One limitation in the design is realized when a plurality of supply tubes are attached to a cap where the number of supply tubes are limited by the surface area of the cap. Furthermore, when a plurality of supply tubes are attached to a cap, attaching each additional tube becomes difficult due to the limitation of space for one's fingers or for tools to enable the attachment of the supply tube to the cap.

Another limitation is realized when removing a cap from a storage container where a gasket is used to create a seal between the cap and the storage container. In practice, when the cap is removed from the storage container the gasket often remains connected to the storage container. In fact, often times the gasket is damaged during removal of the cap and is removed in pieces. These pieces often referred to as gasket debris fall through the fill aperture and into the storage container thereby contaminating the chemical liquid held in the storage container.

SUMMARY OF THE INVENTION

The present invention relates generally, to a universal manifold that enables the delivery and collection of chemical liquid. More specifically, it is known in the art that delivery means the delivery of chemical liquid from a storage container to a machine and collection means the collection of chemical liquids from a machine to a storage container. The present invention provides a universal manifold that enables the delivery and collection of chemical liquid to and from a storage container removing the need to use two separate caps while also ensuring removal of the cap from a storage container simultaneously includes removal of the gasket associated with the cap. The invention will be disclosed in the context of a universal manifold for a storage container that consists of a universal manifold with a plurality of ports for supply lines to be used for delivery and collection of chemical liquid to machine but it should be understood that the invention is useable in various applications where storage containers are required and is not limited to an HPLC machine. One more particularly innovative aspect of the present invention relates to design of the universal manifold such that the universal manifold includes multiple ports for attaching supply tubes while also enabling more space for fingers and tools to attach supply lines to the ports. This is accomplished by providing an angled plane whereby such angle enables the ports to be directed away from the center of the manifold thereby offering additional space for fingers and tools.

Another innovative aspect of the present invention is the universal manifold contains a mating system that is smartly configured to accept ridged universal exchangeable washers made out of plastic or any ridged material that may vary in outside diameter size such that the universal manifold is capable of attaching to variously sized storage containers with variously sized fill apertures by way of a gasket that forms a seal that is designed to form a seal between the universal manifold and the storage container.

Another innovative aspect of the present invention is the gasket securing means of the universal manifold. The gasket securing means consists of a groove that enables the insertion of the interior circumference of a cylindrical gasket into the gasket securing means of the universal manifold thereby increasing the contact surface between the universal manifold and the gasket such that when the cap is removed from the storage container the gasket may overcome any adhesion forces between the gasket and the cap mating surface of the storage container such that the gasket is also removed.

BRIEF DESCRIPTION OF THE DRAWINGS

In the accompanying drawings that form a part of the specification and that are to be read in conjunction therewith and in which like reference numerals are used to indicate like parts in the various views.

DETAILED DESCRIPTION OF THE DRAWINGS

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

A portion of the invention may be described herein in terms of steps. It should be appreciated that such steps may be realized by alternative order.

The overall purpose of the universal manifold described herein is to provide a universal manifold for attaching to variously sized storage containers with variously sized fill apertures for transporting chemical liquid and that also contains multiple ports for attaching supply tubes while providing adequate space for fingers and tools to attach supply tubes to the multiple ports thereof.

Figure 1:
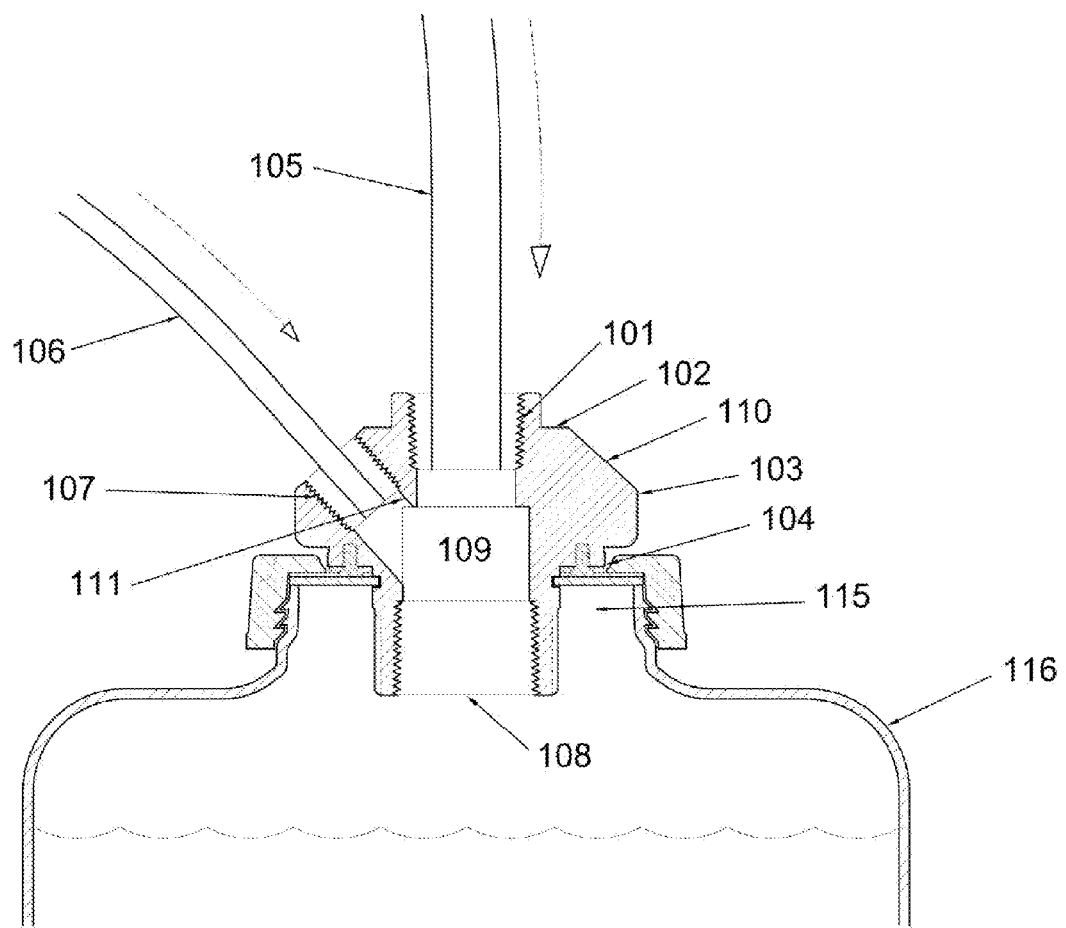
FIG. 1 is an illustration of the universal manifold of the present invention as configured for collecting.

The universal manifold (100) of which is represented in FIG. 1 for the purpose of collecting, where the universal manifold (100) is smartly configured and attached to a storage container (116) to enable the collection of chemical liquids from an HPLC machine to a storage container. (116). Such universal manifold (100) is constructed out of polypropylene, plastic, steel or any ridged material and includes a main receiving port (101) that contains a means for attaching a main supply tube (105) which is located proximal to the main receiving port (101). The main receiving port (101) continues to extend cylindrically through the universal manifold (100) to the distal end (108) of the universal manifold (100) thereby providing a main transportation port (109) for transporting chemical liquid to the distal end (108) of the universal manifold (100). The distal end (108) of the universal manifold (100) is presented to the fill aperture (115) of the storage container (116) such that chemical liquid may travel from the distal end (108) of the universal manifold (100) into the fill aperture (115) of the storage container (116).

On the exterior of the universal manifold (100), near the proximal end, a mating surface (102) is provided which extends perpendicular to the main transportation port (109) and provides a surface where the main receiving port (101) ends. The distal end of the mating surface (102) meets with a sloped multi-port receiving surface (110) which extends away from the main receiving port (101) at an angle and in a manner to offering a plane that extends throughout the circumference of the universal manifold (100) for additional receiving ports. The angle (111) of the sloped multi-port receiving surface (110) in reference to the mating surface (102) is approximately between one hundred and thirty (130) degrees and one hundred and forty five (145) degrees. The multi-port receiving surface (110) includes at least one additional receiving port (107). A number of additional receiving ports may be added to the universal manifold (100) as long as the diameter of the transportation port (109) is not too small as to restrict chemical liquids from adequately traveling during delivery and collection. As further illustrated one end of the additional receiving port (107) which is proximal to the sloped multi-port receiving surface (110) is configured to enable an additional supply tube (106) to attach thereto and be used for collection. The additional receiving port (107) extends perpendicularly away from the sloped multi-port receiving surface (110) and towards the distal end (108) of the universal manifold (100) in a manner that enables the additional transportation port (111) to present an opening into the main transportation port (109). When in use for collecting, the chemical liquid will flow from the additional supply tube ((106) to the additional receiving port (107), through the additional transportation port (111) and into the main transportation port (109), through the distal end (108) and through the fill aperture (115) and into the storage container (116). More specifically, when in use for collecting, the chemical liquid will come into contact with the additional receiving port (107), the additional transportation port (111), the main transportation port (109), and the distal end (108).

Figure 2:
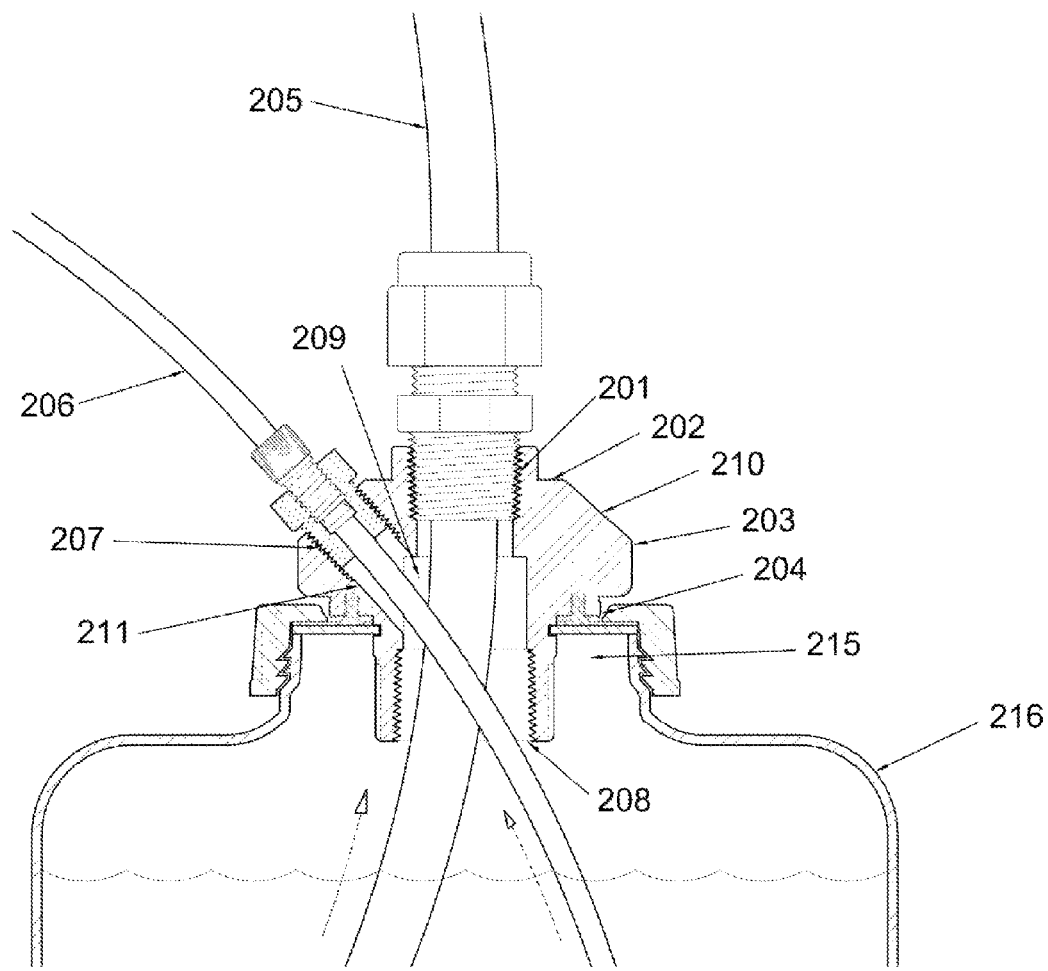
FIG. 2 is an illustration of the universal manifold of the present invention as configured for delivery.

FIG. 2, illustrates universal manifold (200) for the delivery of chemical liquid from a storage container to a machine. When in use for delivery the main receiving port (201) of the universal manifold (200) contains a means for attaching a supply tube (205) whereby the main receiving port (201) is configured to allow the supply tube (205) to pass through the main receiving port (201), through the main transportation port (209), through the distal end (208), through the fill aperture ((215) and into the chemical liquid storage container (216). In use for delivery the chemical liquid through the supply tube (205) and therefore the chemical liquid does not come into contact with the main receiving port (201), the main transportation port (209) and the distal end (208) and the fill aperture (215). Additional receiving port (207), may also be used for delivery as represented in FIG. 2, whereby the additional receiving port (207) is configured to allow the additional supply tube (206) to pass through the additional receiving port (207), through the additional transportation port (211), through the main transportation port (209), through the distal end (208), through the fill aperture (215) and into the storage container (216). In use for delivery, the chemical liquid passes through the additional supply tube (206) therefore the chemical liquid does not come into contact with the additional receiving port (207), additional transportation port (209), the main transportation port (211) and the distal end (208). A number of additional receiving ports may be added to the universal manifold (200) as long as the diameter of the transportation port is not too small as to restrict chemical liquid from adequately traveling during delivery and collection.

Figure 3:
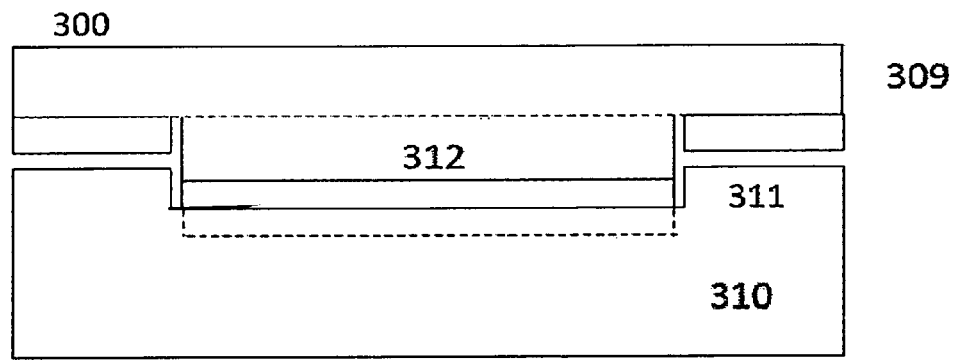
FIG. 3 is a side view illustration of the gasket securing means of the universal manifold

FIG. 3 represents a side view illustration of the gasket securing means of the mating system. More specifically the mating system (300) includes a universal manifold (301) which comprises of a gasket securing means (302) which spans the circumference of the universal manifold (300). The gasket securing means (302) is created by a groove (303) that includes an internal wall (304), a groove ceiling (305), a groove floor (306), and a groove opening (307). The gasket securing means (302) is designed such that the interior circumference of the gasket (308) can be inserted through the groove opening (307) and makes contact with the groove wall (304), the groove ceiling (305) and the groove floor (306). Furthermore, the storage container (310) comprises of a cap mating surface (311) and when the mating system (300) is attached to the storage container (310) the gasket (309) creates a seal between the exchangeable universal mating washer (301) and the cap matting surface (311) of the storage container (310).

The innovative aspect of the mating system is realized and when considering the adhesion forces present between a gasket, which is often made of rubberized material, and the cap mating surface of a storage container. It is now understood that such adhesion forces are caused by pressure placed on the gasket against the cap mating surface when the universal adaptor is attached to the storage container. Additionally, chemical liquid within the storage container may also reside between gasket and the cap mating surface causing chemical adhesion forces between the gasket and the cap mating surface.

Figure 4:
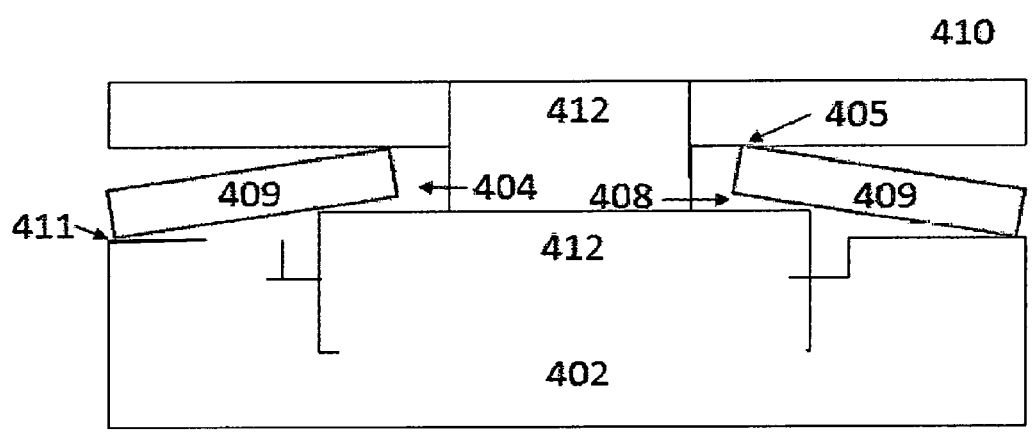
FIG. 4 is a side view illustration of universal manifold of the present representing the gasket securing means in use.

The present invention in practice is further represented in FIG. 4, whereby the universal manifold (410) along with the gasket securing means (404) is being removed from the cap mating surface (411) of the storage container (402). During removal of the universal manifold from the storage container the gasket (409) will continue adhering to the cap mating surface (411) due to the adhesion forces created by pressure and chemical adhesion forces. The gasket will also continue to adhere to the gasket securing means (404) due to the additional contact surface creating adhesion forces. The gasket will loosen first from the ridged universal exchangeable washer (412) of the universal manifold (410). As the universal manifold (410) further separates from the storage container (402) the gasket (409) will begin to pull away from the cap mating surface (411) thereby causing additional adhesion force on the gasket securing means (404). More specifically as the universal manifold (410) further separates from the storage container (402) while the gasket (409) is still adhering to the cap mating surface of the storage container an angle (408) between the gasket (409) and the grove ceiling (405) is created by the washer. This angle creates additional pressure between the interior circumference of the gasket (308)(409) and the groove sealing (405) casing the adhesion force between the gasket (409) and the gasket securing means (404) to increase. This increased adhesion force between the gasket (409) and the gasket securing means (404) enables the gasket to remain attached to the gasket securing means (404) and cause the gasket (409) to separate from the cap mating surface (411) as the angle (408) increases.

Figure 5:
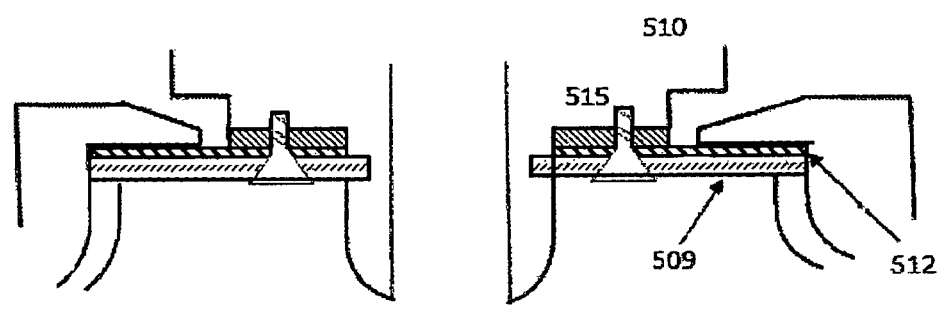
FIG. 5 is an illustration of the ridged exchangeable washer.

In some cases the adhesion forces of the gasket and the cap mating surface are too great to overcome. Another embodiment of the present invention is represented in FIG. 5 to address the stronger adhesion forces that may not be overcome by the gasket securing means. In this embodiment of the present invention at least one screw (515) is provided to fasten the gasket (509) to the rigid universal exchangeable washer (512) of the universal manifold (510)

What is claimed is:

1. A universal manifold system for the delivery and collection of chemical liquid to and from a storage container; the system comprising:
   a manifold, having a groove;
   a storage container;
   a cap, fixed to the storage container;
   an exchangeable ridged washer for securing the universal manifold to variously sized storage containers;
   a gasket, sealing the manifold to the cap; and
   a detractable fastener, for fixing the exchangeable ridged washer to the manifold and the cap.

2. A universal manifold of claim 1, whereby the detractable faster is a screw.

3. A universal manifold system for the delivery and collection of chemical liquid to and from a storage container; the system comprising:
   a manifold;
   a storage container;
   a cap, fixed to the storage container;
   an exchangeable ridged washer, for securing the universal manifold to variously sized storage containers;
   a gasket, sealing the manifold to the cap; and
   a detractable fastener, for fixing the exchangeable ridged washer to the manifold and the cap.

* * * * *